United States Patent [19]

Bossert et al.

[11] 3,968,117

[45] July 6, 1976

[54] 1,4-DIHYDROPYRIDINES

[75] Inventors: Friedrich Bossert; Horst Meyer, both of Wuppertal-Elberfeld; Wulf Vater, Opladen, all of Germany

[73] Assignee: Bayer Aktiengesellschaft, Germany

[22] Filed: Feb. 10, 1975

[21] Appl. No.: 548,521

Related U.S. Application Data

[62] Division of Ser. No. 366,578, June 4, 1973, Pat. No. 3,928,818.

[30] Foreign Application Priority Data

June 10, 1972 Germany............................ 2228363

[52] U.S. Cl...................... 260/295.5 R; 260/294.9; 260/295 R
[51] Int. Cl.$^2$........................................ C07D 213/24
[58] Field of Search.................. 260/294.9, 295.5 A, 260/295.5 R

[56] References Cited
UNITED STATES PATENTS 3,773,773  11/1973  Bossert et al. ............... 260/295.5 R
3,775,422  11/1973  Bossert et al. ................... 260/294.9

*Primary Examiner*—Norman A. Drezin

[57] ABSTRACT

Derivatives of 4-substituted phenyl 1,4-dihydropyridine 3,5-dicarboxylic acids substituted by lower alkyl groups in the 2- and 6-positions, are cardiovascular agents. The compounds, of which 2,6-dimethyl-4-[2-(diethylaminoethoxy)-phenyl]-1,4-dihydropyridine-3,5-dicarboxylic acid 3,5-diethyl ester is a typical example, can be prepared through condensation of a β-dicarbonyl compound with an amine and an aldehyde, of an ylidene-β-ketocarboxylic acid ester, with a β-ketocarbonyl compound and an amine, of an aldehyde, an enamine and a β-ketocarbonyl compound, or through elaboration of the substituent on the phenyl group.

6 Claims, No Drawings

1,4-DIHYDROPYRIDINES

This is a division of application Ser. No. 366,578 filed June 4, 1973.

DETAILED DESCRIPTION

The present invention pertains to new 1,4-dihydropyridines of the formula:

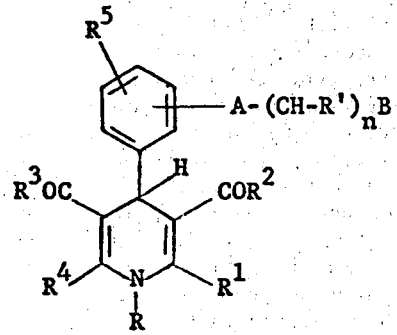

in which
R is hydrogen or a straight or branched chained, saturated or unsaturated aliphatic group;
$R^1$ and $R^4$, which are the same or different, are each hydrogen or straight or branched chained alkyl;
$R^2$ and $R^3$, are the same or different hydrocarbonyl, alkoxy or alkenoxy groups which may be straight-chained, branched or cyclic and which may carry one or two hydroxyl substituents and the carbon chains of which can be interrupted by one or two oxygen atoms;
A is oxygen, sulphur or imino(—NH—);
B is —COOR″ in which R″ is straight or branched alkyl or

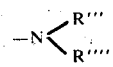

in which R′″ and R″″ when taken independently are the same or different and each is hydrogen or straight or branched chained alkyl, or when taken together with the nitrogen atom to which they are attached are a heterocyclic ring which may contain a further heteroatom;
R′ is hydrogen, hydroxyl or alkyl;
$R^5$ is hydrogen or one or two identical or different substituents selected from alkyl, alkoxy, nitro, acylamino, alkylamino, amino, nitrile and halogen radicals; and
n is an integer from 1 to 4,
and the nontoxic acid addition salts thereof.

The compounds of the present invention can alternatively be depicted by the following formula:

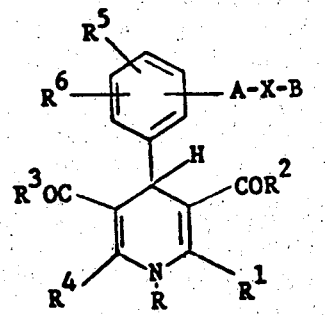

wherein R is hydrogen, lower alkyl or lower alkenyl preferably of 2 to 4 carbon atoms;
each of $R^1$ and $R^4$ is hydrogen or lower alkyl;
each of $R^2$ and $R^3$ is lower alkyl, lower alkenyl preferably of 2 to 4 carbon atoms, furfuryl or an unsubstituted or monosubstituted member selected from the group of lower alkoxy, lower alkenyloxy preferably of 2 to 4 carbon atoms, or lower alkynyloxy preferably of 2 to 4 carbon atoms wherein when substituted the substituent is hydroxyl or lower alkoxy;
A is oxygen, sulphur or imino;
B is carbo-(lower alkoxy) or

in which each of $R^7$ and $R^8$ when taken independently is hydrogen or lower alkyl or when taken together are alkylene of 4 to 6 carbon atoms;
X is lower alkylene or hydroxy-(lower alkylene);
each of $R^5$ and $R^6$ is hydrogen, lower alkyl, lower alkoxy, nitro, halogeno, cyano, amino, lower alkylamino, di-(lower alkyl)amino or acetylamino,
or a nontoxic acid addition salt thereof.

The term lower alkyl denotes a univalent saturated branched or straight hydrocarbon chain containing from 1 to 6 carbon atoms. Representative of such lower alkyl groups are thus methyl, ethyl, propyl, isopropyl, butyl, isobutyl, sec.butyl, tert.butyl, pentyl, isopentyl, neopentyl, tert.pentyl, hexyl, and the like.

The term lower alkenyl denotes a univalent branched or straight hydrocarbon chain containing from 2 to 6 carbon atoms and nonterminal ethylenic unsaturation as, for example, vinyl, allyl, isopropenyl, 2-butenyl, 3-methyl-2-butenyl, 2-pentenyl, 3-pentenyl, 2-hexenyl, 4-hexenyl, and the like.

The term lower alkoxy denotes a lower alkyl group bound to the remainder of the molecule through an oxygen atom as, for example, methoxy, ethoxy, propoxy, isopropoxy, butoxy, isobutoxy, pentoxy and hexoxy, and the like.

The term lower alkenyloxy denotes a lower alkenyl group bound to the remainder of the molecule through an oxygen atom as, for example, vinyloxy, allyloxy, 1-butenoxy, 2-butenoxy, 1-pentenoxy, 2-pentenoxy, 1-hexenoxy, 2-hexenoxy, 3-hexenoxy, and the like.

The term lower alkynyloxy denotes a straight or branched hydrocarbon chain of 3 to 6 carbon atoms bound to the remainder of the molecule through an oxygen atom and containing a triple bond between two carbon atoms other than that bearing the oxygen atom as, for example, propargyloxy, 1-butynoxy, 2-butynoxy, 1-pentynoxy, 2-pentynoxy, 1, 2 or 3-hexynoxy, and the like.

The term lower alkylene denotes a straight or branched divalent hydrocarbon chain of 1 to 6 carbon atoms as, for example, methylene, ethylene, propylene, isopropylene, butylene, isobutylene, tert.butylene, pentylene, isopentylene, tert.pentylene, hexylene, isohexylene, tert.hexylene, and the like.

The term halogen denotes the substituents fluoro, chloro, bromo and iodo.

As indicated, the present invention also pertains to the physiologically acceptable nontoxic acid addition salts of these basic compounds. Such salts include those derived from organic and inorganic acids such as, without limitation, hydrochloric acid, hydrobromic acid, phosphoric acid, sulphuric acid, methane sulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

According to the present invention, the foregoing compounds are prepared by reacting one molar equivalent amount of a β-dicarbonyl compound of the formula:

$$Y-CO-CH_2-CO-Z$$

either i. with a second molar equivalent of a β-dicarbonyl compound as defined above, an amine of the formula:

$$H_2N-R,$$

and an aldehyde of the formula:

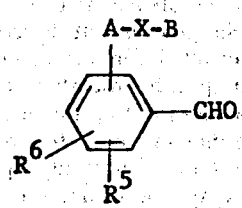

ii. with the amine as defined above and the ylidene formed from a β-dicarbonyl compound as defined above and the aldehyde as defined above; or
iii. with the aldehyde as defined above and the enamine formed from a β-dicarbonyl compound as defined above and the amine as defined above, in which Y is $R^1$ or $R^4$ and Z is $R^2$ or $R^3$ and R, $R^1$, $R^2$, $R^3$, $R^4$, $R^5$, $R^6$, A, B and X are as defined above.

This process can be carried out in the presence of water and/or an inert organic solvent. Alcohols such as ethanol, methanol, or isopropanol, ethers such as dioxane or diethyl ether, or glacial acetic acid, dimethylformamide, dimethylsulphoxide, acetonitrile or pyridine are preferred. The reaction temperature can be varied over a substantial range between about 20° and 150°C, preferably at the boiling point of the solvent. In general the reaction is carried out under normal atmospheric pressure or under elevated pressure.

The β-dicarbonyl compounds used as starting materials for this ring building process are known or can be produced according to known processes as described, for example, in U.S. Pat. No. 2,351,366.

Typical compounds include:
acetylacetone,
heptane-3,5-dione,
formylacetic acid ethyl ester,
formylacetic acid butyl ester,
acetoacetic acid methyl ester,
acetoacetic acid ethyl ester,
acetoacetic acid propyl ester,
acetoacetic acid isopropyl ester,
acetoacetic acid butyl ester,
acetoacetic acid tert.-butyl ester,
acetoacetic acid (α- and β-)-hydroxyethyl esters,
acetoacetic acid (α- and β-)-methoxyethyl esters,
acetoacetic acid (α- and β-)-ethoxyethyl esters,
acetoacetic acid (α- and β-)-n-propoxyethyl esters,
acetoacetic acid allyl ester,
acetoacetic acid propargyl ester,
acetoacetic acid cyclohexyl ester,
propionylacetic acid ethyl ester,
butyrylacetic acid ethyl ester, and
isobutyrylacetic acid ethyl ester.

The amines used in this process are known and include, for example, ammonia, methylamine, ethylamine, propylamine, butylamine, isopropylamine, isobutylamine and allylamine.

The enamines which are, strictly speaking, enamino-β-keto-carbonyl compounds are also known or can be produced according to known methods from the corresponding β-diketo compounds, e.g., Cope, J.A.C.S. 67, 1017 (1945). These include:
2-aminopent-2-en-4-one,
3-aminohept-3-en-5-one,
β-aminocrotonic acid methyl ester,
β-aminocrotonic acid ethyl ester,
β-aminocrotonic acid isopropyl ester,
β-aminocrotonic acid butyl ester,
β-aminocrotonic acid (α- and β-)-methoxymethyl esters,
β-aminocrotonic acid β-propoxyethyl ester,
β-aminocrotonic acid tert.-butyl ester,
β-aminocrotonic acid cyclohexyl ester, and
β-amino-β-ethylacrylic acid ethyl ester.

The ylidene-carbonyl compounds which can also be used to form the dihydropyridine ring are not previously known but can be produced according to known processes; see for example, Org. Reactions XV, 204 et. seq. (1967). Examples of these compounds include:
4-(2-diethylaminoethoxy)-benzylideneacetoacetic acid methyl ester,
3-(2-diethylaminoethylamino)-benzylideneacetoacetic acid isopropyl ester,
2-(methoxycarbonylmethoxy)-benzylideneacetylacetone,
3-(propoxycarbonylmethoxy)-benzylideneacetoacetic acid allyl ester,
3-(3-isopropylamino-2-hydroxypropoxy)-benzylideneacetoacetic acid ethyl ester, and
4-(2-carbethoxyprop-2-oxy)-benzylideneacetoacetic acid β-ethoxyethyl ester.

The aldehydes used according to this process are known or can be produced according to known methods, if appropriate in stages; see for example, Mosettig, Org. Reactions VIII, 218 et seq. (1954). As examples of these aldehydes there may be mentioned:
2-, 3- and 4-formylphenoxyacetic acid ethyl ester,
3-methoxy-4-formylphenoxyacetic acid methyl ester,
2-, 3- and 4-formylphenoxyacetic acid methyl esters,
2-, 3- and 4-formylphenoxy-n-butyric acid ethyl ester,
2-nitro-4-formylphenoxyacetic acid butyl ester,
2-(3-diethylaminopropoxy)benzaldehyde,
4-(3-dipropylamino-2-hydroxypropoxy)benzaldehyde,
3-formylphenoxypropionic acid methyl ester,
2-(3-methylaminopropylamino)-benzaldehyde,
2-, 3- and 4-formylphenoxyacetic acid isopropyl esters, 3-formylphenoxyacetic acid propyl ester,
4-formylphenoxy-acetic acid tert.-butyl ester,
2-methoxy-4-formylphenoxyacetic acid allyl ester,
2-formyl-6-methoxyphenoxyacetic acid allyl ester,
2-formyl-6-isopropylphenoxyacetic acid isopropyl ester,
3-nitro-4-formylphenoxyacetic acid allyl ester,
2-formyl-4-chlorophenoxyacetic acid methyl ester,
2-formyl-4,6-dichlorophenoxyacetic acid ethyl ester,
2-formyl-4-nitrophenoxyacetic acid allyl ester,
2-formyl-4-bromophenoxyacetic acid allyl ester,
2-formyl-4-aminophenoxyacetic acid ethyl ester,
2-formyl-4-acetaminophenoxyacetic acid ethyl ester,
α-(2-, 3- and 4-formylphenoxy)-propionic acid ethyl esters,
2-, 3- and 4-formylphenoxyisobutyric acid methyl esters,
2-, 3- and 4-formylphenoxyisobutyric acid ethyl esters,
2-, 3- and 4-formylphenoxyisobutyric acid propyl esters,
3-methoxy-4-formylphenoxyisobutyric acid ethyl ester,
3-formyl-6-nitrophenoxyisobutyric acid methyl ester.

Alternatively the compounds can be prepared by elaboration of the side chain of the phenyl ring. This can be broadly depicted by reacting a dihydropyridine of the formula:

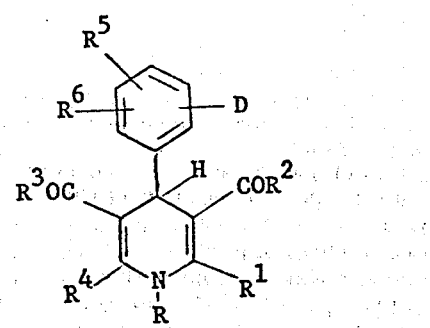

in which R, $R^1$, $R^2$, $R^3$, $R^4$, $R^5$ and $R^6$ are as defined above and D is (i) Hal, (ii) AH or (iii) AXHal with the corresponding reactants (i) HA-X-B, (ii) Hal-X-B or (iii)

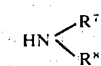

in which A, B, X, $R^7$ and $R^8$ are as defined above and Hal is chloro or bromo, to form the substituent -A-X-B.

This process is preferably carried out in an inert organic solvent at an elevated temperature between about 20° to 150°C in the presence of an acid acceptor such as alkali metal alcoholates, alkali metal and alkaline earth metal carbonates or bicarbonates, pyridine or trialkylamine.

This process includes the use of the equivalent alkali metal salts of the above mentioned phenols, alcohols and mercapto compounds.

The 1,4-dihydropyridines used according to this process are known or can be produced according to conventional processes; see for example, Hantzsch: Liebigs Ann. Chem. 215, 1 (1882), German Offenlegungsschrift No. 1,923,990. Examples of these compounds include:

2,6-dimethyl-4-(3-hydroxyphenyl)-1,4-dihydropyridine-3,5-dicarboxylic acid dimethyl ester,
1,2,6-trimethyl-4-[4-(2,3-ethoxypropoxy)phenyl]-1,4-dihydropyridine-3,5-dicarboxylic acid di(2-methoxyethyl) ester,
1-isopropyl-2,6-diethyl-4-(3-nitro-4-bromophenyl)-1,4-dihydropyridine-3-carboxylic acid methyl ester-5-carboxylic acid isopropyl ester,
2-methyl-6-ethyl-4-(3-amino-6-chlorophenyl)-1,4-dihydropyridine-3,5-dicarboxylic acid difurfuryl ester,
2,6-dimethyl-4-(2-nitro-5-hydroxyphenyl)-1,4-dihydropyridine-3,5-dicarboxylic acid dipropargyl ester,
1,2,6-trimethyl-4-(4-mercaptophenyl)-1,4-dihydropyridine-3,5-dicarboxylic acid dibutyl ester,
2,6-dipropyl-4-[4-(3-diethylamino-2-oxopropoxy)phenyl]-1,4-dihydropyridine-3,5-dicarboxylic acid diethyl ester,
2,6-dimethyl-4-(3-nitro-6-methoxyphenyl)-1,4-dihydropyridine-3,5-dicarboxylic acid di-isopropyl ester, and
2,6-dimethyl-4-[3-nitro-4-(2,3-ethoxypropoxy)-phenyl]-1,4-dihydropyridine-3,5-dicarboxylic acid dimethyl ester.

The compounds according to the invention demonstrate cardiovascular activity. Typical species include:
2,6-dimethyl-4-[3-nitro-4-(3-isopropylamine-2-hydroxypropoxy)phenyl]-1,4-dihydropyridine-3,5-dicarboxylic acid dimethyl ester,
2,6-diethyl-4-[3,5-dimethoxy-4-(3-tert.butylamino-2-hydroxypropoxy)phenyl]-1,4-dihydropyridine-3-carboxylic acid methyl ester-5-carboxylic acid propyl ester;
1-butyl-2,6-dimethyl-4-[2-(2-diethylaminoethylthio)-5-nitrophenyl]-1,4-dihydropyridine-3,5-dicarboxylic acid difurfuryl ester;
1,2,6-trimethyl-4-[2-bromo-5-(3-propylaminobutoxy)-phenyl]-1,4-dihydropyridine-3,5-dicarboxylic acid dipropargyl ester;
2,6-dimethyl-4-[3-methyl-4-(sec.butoxycarbonylmethoxy)phenyl]3,5-diacetyl-1,4-dihydropyridine;
1,2-dimethyl-6-ethyl-4-[2-(2-isopropylamino-1-hydroxyethoxy)-5-chlorophenyl]-1,4-dihydropyridine-3-carboxylic acid ethyl ester-5-carboxylic acid methyl ester; and
2,6-dimethyl-4-[3-isopropoxy-4-(3-ethylamino-2-hydroxypropoxy)phenyl]1,4-dihydropyridine-3,5-dicarboxylic acid dibutyl ester.

As noted above, the compounds of the present invention demonstrate the ability to reduce blood pressure and to effect a dilation of the coronary vessels. They can accordingly be used where either or both of these effects are desired. Thus upon parenteral, oral or sublingual administration, the compounds produce a distinct and long lasting dilation of the coronary vessels which is intensified by a simultaneous nitrite-like effect of reducing the load on the heart. The effect on heart metabolism is thus one of energy saving. In addition, the compounds lower the blood pressure of normotonic and hypertonic animals and can thus be used as antihypertensive agents. These properties can be conveniently observed in well known laboratory models. Thus for example the coronary vessel dilation effect can be observed by measuring the increase in oxygen saturation in the coronary sinus in the narcotized, heart catheterized dog, as shown in the following table:

TABLE

| Compound | Dosage mg/kg | % Increase in O₂ - Saturation | Reversion Time to Initial Value (mins) |
|---|---|---|---|
| 2-6-dimethyl-4-[2-(2-diethylaminoethoxy)-phenyl]-1,4-dihydropyridine-3,5-dicarboxylic acid diethyl ester | 1.0 | 24 | 30 |
| 2,6-dimethyl-4-[4-(2-diethylaminoethowy)-phenyl]-1,4-dihydropyridine-3,5-dicarboxylic acid diisopropyl ester | 3.0 | 30 | 3 |
| 2,6-dimethyl-4-[3-nitro-4-(2-diethylaminoethylamino)-phenyl]-1,4-dihydropyridine-3,5-dicarboxylic acid dimethyl ester | 5.0 | 33 | 20 |
| 2,6-dimethyl-4-[3-(3-isopropylamino-2-hydroxypropoxy)-phenyl]-1,4-dihydropyridine-3,5-dicarboxylic acid diethyl ester | 5.0 | 30 | 3 |
| 1,2,6-trimethyl-4-(3-methoxy-4-ethoxycarbonylmethoxy-phenyl)-1,4-dihydropyridine-3,5-dicarboxylic acid diethyl ester | 1.0 | 31 | 20 |
| 2,6-dimethyl-4-(3-ethoxycarbonylmethoxy-4-methoxyphenyl)-1,4-dihydropyridine-3,5-dicarboxylic acid dimethyl ester | 5.0 | 22 | >120 |
| 2,6-dimethyl-4-(3-ethoxycarbonylmethoxy-4-methoxyphenyl)-1,4-dihydropyridine-3,5-dicarboxylic acid diethyl ester | 5.0 | 25 | >30 |
| 2,6-dimethyl-4-(3-methoxy-4-ethoxycarbonylmethoxy-phenyl)-1,4-dihydropyridine-3,5-dicarboxylic acid dimethyl ester | 5.0 | 34 | >120 |
| 2,6-dimethyl-4-(3-methoxy-4-ethoxycarbonylmethoxy-phenyl)-1,4-dihydropyridine-3,5-dicarboxylic acid diethyl ester | 5.0 | 22 | 45 |
| 2,6-dimethyl-4-(2-ethoxycarbonylmethoxy-5-nitro-phenyl)-1,4-dihydropyridine-3,5-dicarboxylic acid diethyl ester | 0.1 | 22 | 45 |
| 2,6-dimethyl-4-(2-ethoxycarbonylmethoxy-5-nitro-phenyl)-1,4-dihydropyridine-3,5-dicarboxylic acid dimethyl ester | 0.1 | 15 | >60 |
| 2,6-dimethyl-4-(2-ethoxycarbonylmethoxy-5-nitro-phenyl)-1,4-dihydropyridine-3,5-dicarboxylic acid diisopropyl ester | 0.2 | 24 | 45 |
| 2,6-dimethyl-4-(2-ethoxycarbonylmethoxy-5-bromo-phenyl)-1,4-dihydropyridine-3,5-dicarboxylic acid diethyl ester | 0.5 | 22 | 10 |

In addition to the effect on blood pressure and coronary vessels, the compounds also lower the excitability of the stimulus formation and excitation conduction system within the heart so that an antifibrillation action is observed at therapeutic doses. The tone of the smooth muscle of the vessels is also greatly reduced. This vascular-spasmolytic action can be observed in the entire vascular system as well as in more or less isolated and circumscribed vascular regions such as the central nervous system. In addition, a strong muscular-spasmolytic action is manifested in the smooth muscle of the stomach, the intestinal tract, the urogenital tract and the respiratory system. Finally, there is some evidence that the compounds influence the cholesterol level and lipid level of the blood. These effects complement one another and the compounds are thus highly desirable as pharmaceutical agents to be used in the treatment of hypertension and conditions characterized by a constriction of the coronary blood vessels.

Pharmaceutical compositions for effecting such treatment will contain a major or minor amount, e.g. from 95 to 0.5% of at least one 1,4-dihydropyridine as herein defined in combination with a pharmaceutical carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e. physically discrete units containing a predetermined amount of the drug corresponding to a fraction of multiple of the dose which is calculated to produce the desired therapeutic response. The dosage units can contain one, two, three, four or more single doses or, alternatively, one-half, third or fourth of a single dose. A single dose preferably contains an amount sufficient to produce the desired therapeutic effect upon administration of one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the daily dose will be from about 0.01 to about 10 mg/kg, preferably 0.1 to 5 mg/kg, when administered parenterally and from about 1 to about 100 mg/kg, preferably 5 to 50 mg/kg, when administered orally. In some instances a sufficient therapeutic effect can be obtained at lower doses while in others, larger doses will be required.

Oral administration can be effected utilizing solid and liquid dosage unit forms such as powders, tablets, dragees, capsules, granulates, suspensions, solution, and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitor esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax, or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

The following examples will serve to further typify the nature of the present invention through the presentation of specific embodiments. These examples should not be construed as a limitation on the scope of the invention since the subject matter regarded as the invention is set forth in the appended claims.

EXAMPLE 1

2-6-Dimethyl-4-[2-(2-diethylaminoethoxy)-phenyl]-1,4-dihydropyridine-3,5-dicarboxylic acid diethyl ester.

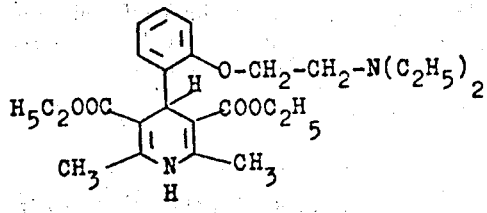

A solution of 22 g of 2-(2-diethylaminoethoxy)-benzaldehyde (boiling point 134°/4), 28 ml of acetoacetic acid ethyl ester and 11 ml of concentrated ammonia in 40 ml of alcohol is heated at reflux for 5 hours. After evaporation, white crystals of melting point 79°–81°C are obtained. Yield: 75% of theory.

EXAMPLE 2

2,6-Dimethyl-4-[4-(2-diethylaminoethoxy)-phenyl]-1,4-dihydropyridine-3,5-dicarboxylic acid diethyl ester.

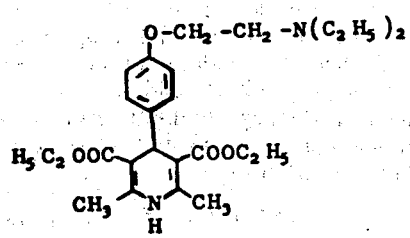

After heating a solution of 10 g of 4-(2-diethylaminoethoxy)-benzaldehyde (boiling point 128°/4), 12 ml of acetoacetic acid ethyl ester and 5 ml of ammonia under reflux for 6 hours, the mixture is evaporated and the residue, which solidifies to white crystals after prolonged standing, is recrystallized from petroleum ether to m.p. 101°–103°C. Yield: 70% of theory.

a. In the same manner, acetoacetic acid isopropyl ester yields 2,6-dimethyl-4-[4-(2-diethylaminoethoxy)-phenyl]-1,4-dihydropyridine-3,5-dicarboxylic acid diisopropyl ester of melting point 113°–115°C (ligroin/petroleum ether). Yield: 75% of theory.

EXAMPLE 3

2,6-Dimethyl-4-[3-(2-diethylaminoethylamino)-phenyl]-1,4-dihydropyridine-3,5-dicarboxylic acid diethyl ester.

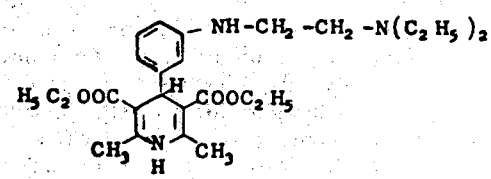

Thirty-four grams of 2,6-dimethyl-4-(3'-aminophenyl)-1,4-dihydropyridine-3,5-dicarboxylic acid diethyl ester and 15 ml of 2-diethylaminoethyl chloride are heated to 180° (internal temperature) for 5 minutes. The mixture is subsequently taken up in hot water and, after adding ice and alkali, extracted with ether. The hydrochloride salt of melting point 140 - 142°C is obtained by treatment with ethereal hydrogen chloride. Yield: 90% of theory.

EXAMPLE 4

2,6-Dimethyl-4-[3-(2-diethylaminoethylamino)-6-chlorophenyl]-1,4-dihydropyridine-3,5-dicarboxylic acid diethyl ester.

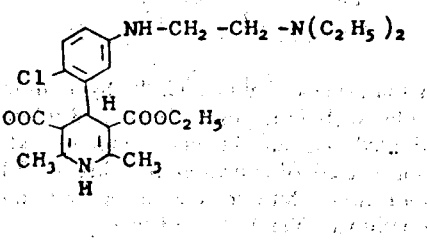

Thirty grams of 2,6-dimethyl-4-(3-amino-6-chlorophenyl)-1,4-dihydropyridine-3,5-dicarboxylic acid diethyl ester (melting point 210°) and 15 ml of 2-diethylaminoethyl chloride are heated for 15 minutes to about 200° and the mixture is taken up in hot water, rendered alkaline after addition of ice and extracted with ether.

Treatment with hydrogen chloride in ether yields the hydrochloride salt, m.p. 169°-171°C (rose-red crystals). Yield: 85% of theory.

EXAMPLE 5

2,6-Dimethyl-4-[3-nitro-4-(2-diethylaminoethylamino)phenyl]-1,4-dihydropyridine-3,5-dicarboxylic acid dimethyl ester.

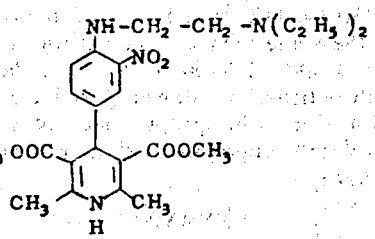

Ten grams of 2,6-dimethyl-4-(3-nitro-4-chlorophenyl)-1,4-dihydropyridine-3,5-dicarboxylic acid dimethyl ester and 8 g of 2-(diethylamino)ethylamine are heated to 100° (external temperature) overnight. After cooling, ether is added and the product collected by filtration to yield orange crystals of melting poing 161°C after recrystallization from 80 ml of methanol. Yield: 80% of theory.

EXAMPLE 6

2,6-Dimethyl-4-[3-(3-isopropylamino-2-hydroxypropoxy)-phenyl]-1,4-dihydropyridine-3,5-dicarboxylic acid diethyl ester.

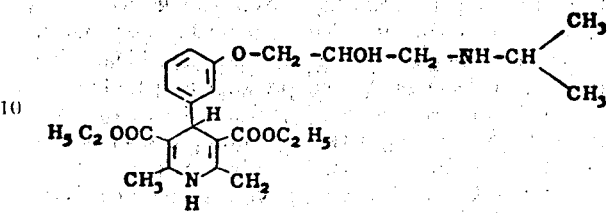

After adding 3 g of isopropylamine in 40 ml of alcohol, 9 g of 2,6-dimethyl-4-[3-(2,3-epoxypropoxy)-phenyl]-1,4-dihydropyridine-3,5-dicarboxylic acid diethyl ester are heated overnight at reflux. The mixture is concentrated and treated with acetone-ether to precipitate the hydrochloride salt as white crystals of m.p. 121°-124°C. Yield: 85% of theory.

2,6-Dimethyl-4-[3-(2,3-epoxypropoxy)-phenyl]-1,4-dihydropyridine-1,4-dicarboxylic acid diethyl ester can be obtained, as white crystals of melting point 116°C (benzene), by heating 34 g of 2,6-dimethyl-4-(3-hydroxyphenyl)-1,4-dihydropyridine-3,5-dicarboxylic acid diethyl ester with 28 g of epichlorohydrin and 14 g of potassium carbonate in 250 ml of acetone under reflux for 14 hours.

EXAMPLE 7

1,2,6-Trimethyl-4-[4-(3-isopropylamino-2-hydroxypropoxy)-phenyl]-1,4-dihydropyridine-3,5-dicarboxylic acid dimethyl ester.

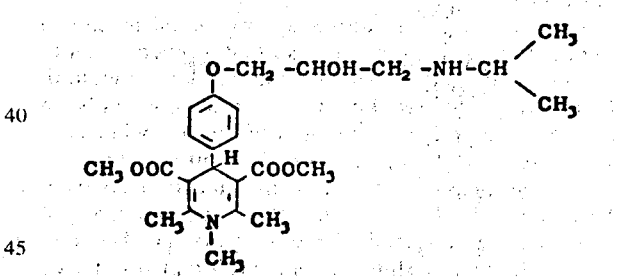

Eleven grams of 1,2,6-trimethyl-4-[4-(2,3-epoxypropoxy)-phenyl]-1,4-dihydropyridine-3,5-dicarboxylic acid dimethyl ester (melting point 126°), 3 g of isopropylamine and 40 ml of alcohol are heated at reflux overnight, concentrated in vacuo and treated with acetone. The product precipitates as the hydrochloride salt, white crystals of melting point 211°-212°C, in a yield of 90% of theory.

EXAMPLE 8

2,6-Dimethyl-4-(2-methoxycarbonylmethoxyphenyl)-1,4-dihydropyridine-3,5-dicarboxylic acid dimethyl ester.

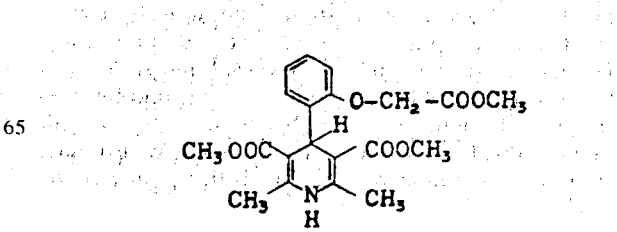

After heating 10 g of 2-formylphenoxyacetic acid methyl ester, 5 g of ammonium acetate and 15 ml of acetoacetic acid methyl ester in 30 ml of pyridine at 100° for several hours, the mixture is poured into ice water. Beige crystals of melting point 153°–155°C are thus formed in a yield of 65% of theory.

EXAMPLE 9

2,6-Dimethyl-4-(2-isopropoxycarbonylmethoxyphenyl)-1,4-dihydropyridine-3,5-dicarboxylic acid diethyl ester.

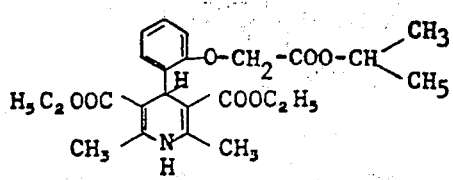

After heating a solution of 11 g of 2-formylphenoxyacetic acid isopropyl ester, 14 ml of acetoacetic acid ethyl ester and 6 g of ammonium acetate in 40 ml of pyridine to 100° for several hours, the mixture is poured into water and taken up in ether to yield an oil.
Yield: 90% of theory.
a. In the same manner, 2-formylphenoxyacetic acid propyl ester yields 2,6-dimethyl-4-(2-propoxycarbonylmethoxyphenyl)-1,4-dihydropyridine-3,5-dicarboxylic acid dipropyl ester (oil).
Yield: 70% of theory

EXAMPLE 10

2,6-Dimethyl-4-(2-ethoxycarbonylmethoxyphenyl)-1,4-dihydropyridine-3,5-dicarboxylic acid dimethyl ester.

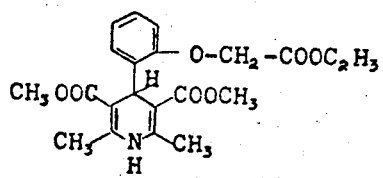

After heating 10.4 g of 2-formylphenoxyacetic acid ethyl ester, 14 ml of acetoacetic acid methyl ester and 5 g of ammonium acetate in 30 ml of pyridine at about 100° for 5 hours, the mixture is poured into water. After standing overnight, the product is collected by filtration to yield white crystals of melting point 145° (ether).
Yield: 75% of theory.

EXAMPLE 11

2,6-Dimethyl-4-(2-ethoxycarbonylmethoxyphenyl)-1,4-dihydropyridine-3,5-dicarboxylic acid diisopropyl ester.

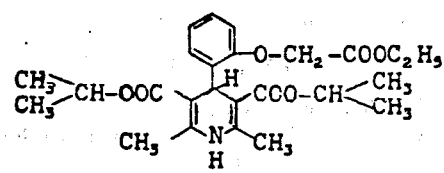

A mixture of 10.4 g of 2-formylphenoxyacetic acid ethyl ester, 16 ml of acetoacetic acid isopropyl ester and 5 g of ammonium acetate in 30 ml of pyridine is heated to from 90 to 100°C for 8 hours. The mixture is subsequently introduced into water. This mixture is then extracted with ether end, after washing and drying, the ethereal extracts are evaporated to yield an oil.
Yield: 90% of theory.

EXAMPLE 12

2,6-Dimethyl-4-(3-ethoxycarbonylmethoxyphenyl)1,4-dihydropyridine-3,5-dicarboxylic acid diethyl ester

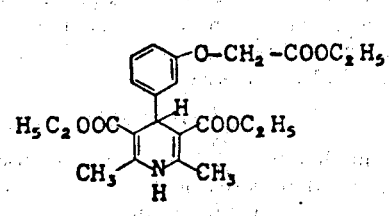

A mixture 10.4 g of 3-formylphenoxyacetic acid ethyl ester, 14 ml of acetoacetic acid ethyl ester and 5 g of ammonium acetate in 30 ml of pyridine is heated for 4 hours at approximately 100°. It is then added to water which is extracted with ether to yield yellow crystals of melting point 108°C (alcohol-ether).
Yield: 90% of theory.

EXAMPLE 13

2,6-Dimethyl-4-[4-(2-ethoxycarbonylprop-2-oxy)-phenyl]-1,4-dihydropyridine-3,5-dicarboxylic acid diethyl ester.

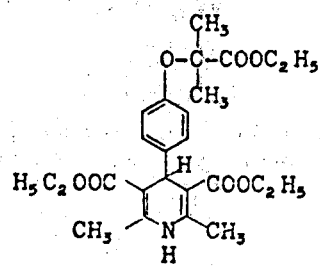

A solution of 2.3 g of sodium in 120 ml of alcohol is treated with 34.5 g of 2,6-dimethyl-4-(4-hydroxyphenyl)-1,4-dihydropyridine-3,5-dicarboxylic acid diethyl ester and with 21.5 g of α-bromo-isobutyric acid ethyl ester added from a dropping funnel. The mixture is boiled overnight, added to water and extracted with ether. White crystals of melting point 215°C (benzene) are obtained from the evaporation residue.
Yield: 60% of theory.

EXAMPLE 14

1,2,6-Trimethyl-4-(3-methoxy-4-ethoxycarbonylmethoxyphenyl)-1,4-dihydropyridine-3,5-dicarboxylic acid diethyl ester.

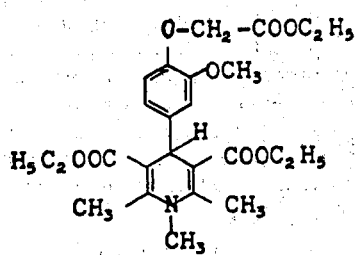

After heating 12 g of 3-methoxy-4-formylphenoxyacetic acid ethyl ester, 14 ml of acetoacetic acid ethyl ester and 6 g of methylamine hydrochloride in 30 ml of pyridine at 90° to 100°C for 2 hours, the mixture is added to water and the product collected by filtration. Yellow crystals of melting point 84°–85°C are obtained in a yield of 73% of theory.

EXAMPLE 15

1,2,6-Trimethyl-4-[4-(2-ethoxycarbonylprop-2-oxy)-phenyl]-1,4-dihydropyridine-3,5-dicarboxylic acid dimethyl ester.

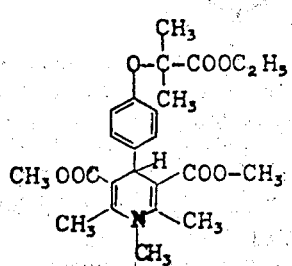

A solution of 24 g of α-(4-formylphenoxy)isobutyric acid ethyl ester, 25 ml of acetoacetic acid methyl ester and 8 g of methylamine hydrochloride in 60 ml of pyridine is heated for 4 hours at approximately 100°C and introduced into water. The product is filtered off and yellow crystals (20 g) of melting point 94°C (alcohol) are obtained.

Yield: 56% of theory.

EXAMPLE 16

1,2,6-Trimethyl-4-[4-(2-ethoxycarbonylprop-2-oxy)-phenyl]-1,4-dihydropyridine-3,5-dicarboxylic acid diethyl ester.

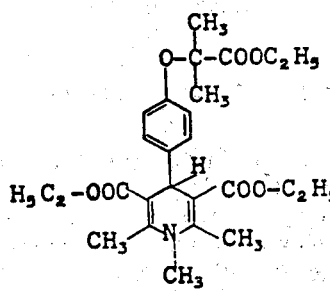

After heating 8 g of α-(4-formylphenoxy)isobutyric acid ethyl ester, 10 ml of acetoacetic ethyl ester and 3 g of methylamine hydrochloride in 30 ml of pyridine at 90° to 100°C for 4 hours, the mixture is poured into water and the product collected by filtration and recrystallized from ligroin to yield white crystals of melting point 88°C.

Yield: 60% of theory.

EXAMPLE 17

2,6-Dimethyl-4-(3-ethoxycarbonylmethoxy-4-methoxyphenyl)-1,4-dihydropyridine-3,5-dicarboxylic acid dimethyl ester.

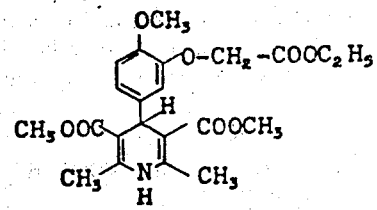

A solution of 12 g of 4-methoxy-3-formylphenoxyacetic acid ethyl ester, 14 ml of acetoacetic acid methyl ester and 5 g of ammonium acetate in 30 ml of pyridine is heated at 90° to 100°C for 6 hours and then poured into water. Light yellow crystals of melting point 170°C are obtained after recrystallization from alcohol.

Yield: 68% of theory.

a. In the same manner, acetoacetic acid ethyl ester yields 2,6-dimethyl-4-(3-ethoxycarbonylmethoxy-4-methoxyphenyl)-1,4-dihydropyridine-3,5-dicarboxylic acid diethyl ester of melting point 114°C. Yield: 58% of theory.

EXAMPLE 18

2,6-Dimethyl-4-(3-methoxy-4-ethoxycarbonylmethoxyphenyl)-1,4-dihydropyridine-3,5-dicarboxylic acid dimethyl ester.

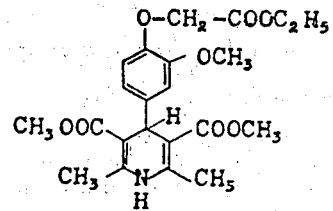

Twelve grams of 3-methoxy-4-formylphenoxyacetic acid ethyl ester, 14 ml of acetoacetic acid methyl ester and 5 g of ammonium chloride in 30 ml of pyridine are heated at 90° to 100°C for 4 hours. The mixture is poured into water and the solid is recrystallized from methanol to yield yellow crystals of melting point 172°–174°C.

Yield: 90% of theory.

a. In the same manner, acetoacetic acid ethyl ester yields 2,6-dimethyl-4-(3-methoxy-4-ethoxycarbonylmethoxyphenyl)-1,4-dihydropyridine-3,5-dicarboxylic acid diethyl ester of melting point 107°C.

Yield: 62% of theory.

EXAMPLE 19

2,6-Dimethyl-4-(2-ethoxycarbonylmethoxy-5-nitrophenyl)-1,4-dihydropyridine-3,5-dicarboxylic acid diethyl ester.

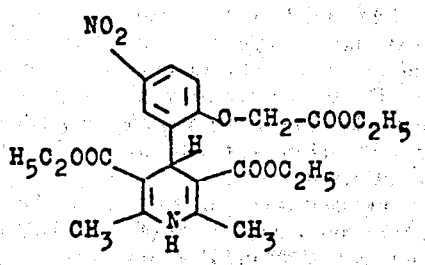

A mixture of 12.5 g of 2-formyl-4-nitrophenoxyacetic acid ethyl ester, 14 ml of acetoacetic acid ethyl ester and 5 g of ammonium acetate in 40 ml of pyridine is heated at approximately 100°C for 1½ hours. The mixture is then poured into water. The solid which forms is recrystallized from ethanol to yield yellow crystals of melting point 175°C.

Yield: 65% of theory.

a. In the same manner, acetoacetic acid methyl ester yields 2,6-dimethyl-4-(2-ethoxycarbonylmethoxy-5-nitrophenyl)-1,4-dihydropyridine-3,5-dicarboxylic acid dimethyl ester of melting point 185°C (alcohol).

Yield: 70% of theory.

b. With acetoacetic acid isopropyl ester, 2,6-dimethyl-4-4-(2-ethoxycarbonylmethoxy-5-nitrophenyl)-1,4-dihydropyridine-3,5-dicarboxylic acid diisopropyl ester of melting point 124°C is obtained.

Yield: 45% of theory.

EXAMPLE 20

2,6-Dimethyl-4-(2-ethoxycarbonylmethoxy-5-bromophenyl)-1,4-dihydropyridine-3,5-dicarboxylic acid diethyl ester.

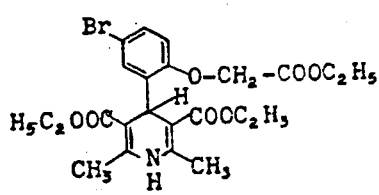

After heating 18 g of 2-formyl-4-bromophenoxyacetic acid ethyl ester, 18 ml of acetoacetic acid ethyl ester and 8 g of ammonium acetate in 50 ml of pyridine for 4 hours, the mixture is poured into water. Golden yellow crystals of melting point 153°–154°C are obtained after recrystallization from alcohol.

Yield: 60% of theory.

EXAMPLE 21

1,2,6-Trimethyl-4-(2-ethoxycarbonylmethylmercapto-5-nitrophenyl)-1,4-dihydropyridine-3,5-dicarboxylic acid dimethyl ester.

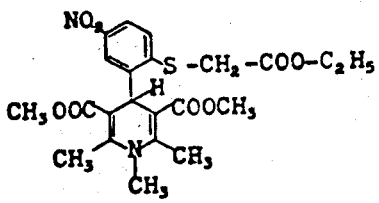

A solution of 19.7 g of 1,2,6-trimethyl-(2-chloro-5-nitrophenyl)-1,4-dihydropyridine-3,5-dicarboxylic acid dimethyl ester (melting point 190°C) in 200 ml of alcohol is heated to reflux and 60 ml of a solution of 2.3 g of sodium in 100 ml of alcohol, together with 13.2 g of mercaptoacetic acid ethyl ester, are added thereto. The mixture is refluxed for 15 hours and thereafter filtered and evaporated. The precipitate obtained after adding a little ether is recrystallized from methanol to yield yellow crystals of melting point 118°C.

Yield: 72% of theory.

EXAMPLE 22

2,6-Dimethyl-4-[3-methoxy-4-(3-dimethylaminopropoxy)phenyl]-1,4-dihydropyridine-3,5-dicarboxylic acid diethyl ester.

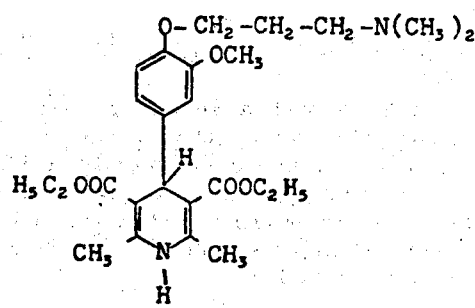

A solution of 2.3 g of sodium in 100 ml of ethanol is added to a warm solution of 37.5 g of 2,6-dimethyl-4-(3-methoxy-4-hydroxyphenyl)-1,4-dihydropyridine-3,5-dicarboxylic acid diethyl ester (melting point 172°C) in 300 ml of ethanol. The mixture is heated at reflux and 15 g of 3-dimethylaminopropyl chloride are added dropwise. After refluxing for several hours, the mixture is filtered hot, the residue being washed with alcohol, and the filtrate is evaporated in vacuo to yield yellow crystals of melting point 62°C after recrystallization from ligroin-petroleum ether.

Yield: 75% of theory.

EXAMPLE 23

1-n-Butyl-2,6-dimethyl-4-(2-ethoxycarbonylmethoxy-5-nitrophenyl)-1,4-dihydropyridine-3,5-dicarboxylic acid diethyl ester.

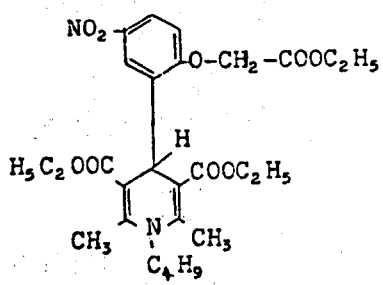

A mixture of 12.7 g of 2-formyl-4-nitrophenoxyacetic acid ethyl ester, 14 ml of acetoacetic acid ethyl ester and 6 ml of n-butylamine in 40 ml of ethanol are heated at reflux overnight. Upon prolonged cooling, yellow crystals of melting point 88°–90°C are obtained.

Yield: 60% of theory.

What is claimed is:

1. A compound of the formula:

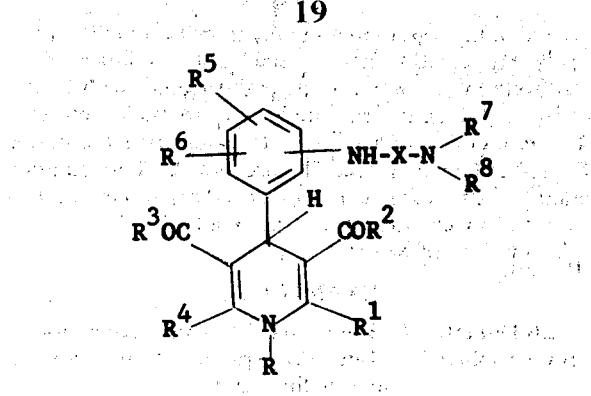

wherein
R is hydrogen, lower alkyl or alkenyl of 2 to 4 carbon atoms;
each of $R^1$ and $R^4$ is hydrogen or lower alkyl;
each of $R^2$ and $R^3$ is lower alkyl, alkenyl of 2 to 4 carbon atoms, furfuryl or a member selected from the group consisting of lower alkoxy, alkenyloxy of 2 to 4 carbon atoms and alkynyloxy of 2 to 4 carbon atoms which is unsubstituted or substituted by hydroxy or lower alkoxy;

each of $R^5$ and $R^6$ is hydrogen, lower alkyl, lower alkoxy, nitro, halogeno, cyano, amino, lower alkylamino, di-(lower alkyl)amino or acetylamino;
$R^7$ and $R^8$ are each hydrogen or lower alkyl; and
X is lower alkylene or hydroxy-(lower alkylene); or a nontoxic pharmaceutically acceptable acid addition salt thereof.

2. A compound according to claim 1 wherein R is hydrogen or lower alkyl; each of $R^1$ and $R^4$ is lower alkyl, and each of $R^2$ and $R^3$ is lower alkoxy.

3. A compound according to claim 1 wherein each of $R^5$ and $R^6$ is hydrogen, lower alkoxy, nitro, halogeno, cyano or amino.

4. The compound according to claim 1 which is 2,6-dimethyl-4-[3-(2-diethylaminoethylamino)-phenyl]-1,4-dihydropyridine-3,5-dicarboxylic acid diethyl ester.

5. The compound according to claim 1 which is 2,6-dimethyl-4-[3-(2-diethylaminoethylamino)-6-chlorophenyl]-1,4-dihydropyridine-3,5-dicarboxylic acid diethyl ester.

6. The compound according to claim 1 which is 2,6-dimethyl-4-[3-nitro-4-(2-diethylaminoethylamino)-phenyl]-1,4-dihydropyridine-3,5-dicarboxylic acid dimethyl ester.

* * * * *